United States Patent [19]

Eggensperger et al.

[11] Patent Number: 5,122,541

[45] Date of Patent: Jun. 16, 1992

[54] SPRAYABLE SURFACE DISINFECTANT

[75] Inventors: Heinz Eggensperger; Ute Eggers-Maass; Bernd Löwer, all of Hamburg; Holger Brill, Norderstedt; Helmut Nolte, Tangstedt, all of Fed. Rep. of Germany

[73] Assignee: Sterling Drug, Inc., New York, N.Y.

[21] Appl. No.: 482,439

[22] Filed: Feb. 20, 1990

[30] Foreign Application Priority Data

Feb. 18, 1989 [DE] Fed. Rep. of Germany ....... 3905063

[51] Int. Cl.$^5$ .................... A01N 37/00; A01N 41/10; A01N 31/00; A01N 35/00
[52] U.S. Cl. .................................. 514/578; 514/709; 514/724; 514/705; 514/557
[58] Field of Search ............... 514/705, 709, 724, 557, 514/578; 254/107

[56] References Cited

U.S. PATENT DOCUMENTS 4,759,867  7/1988  Choy ................................... 252/143
4,975,217 12/1990  Brown-Skrobot .................. 252/107

FOREIGN PATENT DOCUMENTS 1244759 11/1988  Canada .............................. 167/19.1

Primary Examiner—Frederick E. Waddell
Assistant Examiner—Gregory Hook
Attorney, Agent, or Firm—John R. Everett

[57] ABSTRACT

A sprayable aqueous disinfecting composition for disinfecting hard surfaces comprising 20 to 30% by weight of a mixture of ethyl alcohol and isopropyl alcohol in a weight ratio of 1:2 to 2:1, 0.05 to 0.5% by weight of a mixture of a primary or secondary $C_{10-18}$-alkane sulfonate and/or a $C_{10-18}$-alkyl sulfate with a $C_{10-14}$-alkyl ether sulfate, a pH adjusting agent for adjusting the pH in the range of 2 to 6 or 8 to 12, and the remainder to 100% by weight water.

7 Claims, No Drawings

SPRAYABLE SURFACE DISINFECTANT

BACKGROUND OF THE INVENTION (a) Field of the Invention

The invention relates to a disinfectant composition for disinfecting surfaces, more particularly to such a composition which is sprayable and is based on a lower aliphatic monohydric alcohol, an alkyl sulfate or sulfonate, an alkyl ether sulfate, a pH adjusting agent and water.

(b) Information Disclosure Statement

Canadian Patent No. 1,244,759 disclosed microbicidal compositions which may be formulated as solids or aqueous liquids comprising as essential active ingredients certain organic acids and an alkali metal or substituted ammonium salt of a primary or secondary $C_{8-18}$ alkyl sulfate or sulfonate in the ratio of the organic acid to the sulfate or sulfonate of 50:1 to 1:50. In liquid form the pH of the composition should be between 0.1 and 0.5. Certain alcohols such as ethyl alcohol, n-propyl alcohol, isopropyl alcohol and 1,2-propanediol may be employed to dissolve particular organic acids having limited solubility and to provide faster drying of the compositions after application to a surface. Specific compositions are exemplified containing 5% of 1,2-propanediol and 15 and 20% of ethyl alcohol.

It is generally known to employ alcoholic spray disinfectants including an anionic surfactant as a wetting agent.

The aforementioned microbiocidal compositions and alcoholic spray disinfectants have the advantage of being free from aldehydes, phenols and other controversial substances. However, the compositions disclosed in Canadian Patent No. 1,244,759 when formulated as solids and diluted with water for end use, have the drawback that they dry relatively slowly on the treated surfaces; when used at low but acceptable concentrations, they take a relatively long time to be effective; and when used at correspondingly higher concentrations in order to shorten the time to effectiveness, they leave behind residues or can damage the treated surface.

In the case of the known disinfectant alcoholic sprays, due to their relatively high content of alcohol, although they are effective in a short period of time and dry rapidly, they have the drawback that, in addition to having poor cleansing action, they can, on prolonged use, harm the surfaces to be disinfected, particularly plastic surfaces such as polyester and polyacrylate surfaces, and give rise to cracks and embrittlement. Furthermore, the handling of disinfectants having a high content of alcohol can cause problems due to their relatively low flashpoint and the hazards associated therewith.

SUMMARY OF THE INVENTION

It is an object of the invention to provide a sprayable surface disinfectant in ready-to-use form having rapid bactericidal and fungicidal activity, even at low temperatures, good cleansing action, good compatibility with the surfaces to be treated, a low content of alcohol, a relatively high flash point and a low allergenic potential, even on prolonged use, and which dries rapidly and leaves very little residue when applied to surfaces to be disinfected.

Surprisingly, it has been found that contrary to current opinion, adequate surface disinfection is achieved with much lower concentrations of aliphatic alcohols, in the range of 20 to 35% by weight, if only small amounts of a combination of a primary or secondary alkane sulfonate or alkyl sulfate in combination with equally small amounts of an alkyl ether sulfate are employed, of course depending on observing the very different parameters with respect to the components on the one hand and the weight ratios of these components on the other hand.

Thus the invention provides an aqueous surface disinfectant composition comprising a) from about 20 to about 35% by weight of a mixture of ethyl alcohol and isopropyl alcohol in a weight ratio of ethyl alcohol to isopropyl alcohol of from about 1:2 to about 2:1; b) from about 0.05 to about 0.5% by weight of a mixture of anionic surfactants comprising b-1) a salt of a primary or secondary alkane sulfonic acid or alkyl sulfate having from 10 to 18 carbon atoms in the alkane and alkyl radicals, and b-2) a salt of an alkyl ether sulfate having from 10 to 14 carbon atoms in the alkyl radical; c) an acidifying agent or an alkalizing agent in an amount sufficient to provide a pH within the range of from about 2 to about 6 or about 8 to about 12; and the remainder to 100% by weight water; wherein the weight ratio of (b-1) to (b-2) is from about 10:1 to 2:1 and of (a) to (b) is from about 300:1 to about 50:1.

The aqueous surface disinfectant compositions of the invention are especially useful for surface disinfection in hospitals, homes and medical surgeries, particularly in highly soiled areas where rapid action and rapid drying are essential because of the large number of persons passing through, for example, in ambulances, public baths and saunas, also in semi-medical establishments such as chiropodists' parlors, sunbathing studios, hairdressing and massage parlors, as well as in the field of catering and accomodations in kitchens and hotels, and for the sterilization of equipment, such as telephones, which are in frequent use by many persons.

DETAILED DESCRIPTION OF THE INVENTION INCLUDING THE PREFERRED EMBODIMENTS

The aqueous surface disinfectant composition comprises as essential components ethyl alcohol, isopropyl alcohol, an alkane sulfonate or alkyl sulfate, an alkyl ether sulfate, a pH adjusting agent and water.

Even if no doubt exists regarding their microbiological activity, the use only of either n-propyl alcohol (1-propanol) or isopropyl alcohol (2-propanol) is precluded because of the musty heavy odor of the former and the lingering pungent odor of the latter. However, isopropyl alcohol can be used if combined with ethyl alcohol in the weight ratio of from about 1:2 to about 2:1, preferably from about 1:1.4 to about 1.5:1. Surprisingly it has been found that the best results are obtained if the mixture of ethyl and isopropyl alcohols is employed at a concentration in the aqueous disinfectant composition of from about 20 to about 35% by weight, preferably from about 25 to about 30% by weight. Use of the specified concentrations and weight ratios of the ethyl and isopropyl alcohols is important because the tendency toward stress corrosion cracking in polyacrylic surfaces (plexiglass) used, for example, for sunbathing bench-rest surfaces, increases in the order of water, ethyl alcohol, isopropyl alcohol.

Any of the well known primary or secondary alkane sulfonates or alkyl sulfates having from about 10 to about 18 carbon atoms in the alkane and alkyl radicals, or mixtures thereof, can be employed. Such sulfonates and sulfates are commercially availabale or can be prepared by known procedures.

The sulfonates and sulfates can be in the form of alkali metal, alkaline earth metal, ammonium and substituted ammonium, e.g., monoethanol-, diethanol- and triethanolammonium and methyl-, ethyl-isopropyl-, dimethyl-, diethyl-, tri-methyl- and triethylammonium, salts. Particularly suitable alkyl sulfates are those sold under the trademark "Texapon", such as sodium, magnesium, ammonium, monoethanolammonium and triethanolammonium lauryl sulfate and sodium cetyl sulfate. Particularly suitable alkane sulfonates are those sold under the trademark "Mersolates", "Hostapur SAS" and "Marlon PS" with $C_{15}$ or $C_{13}$ and $C_{10}$ to $C_{18}$ or $C_{15}$ to $C_{17}$ cuts.

The alkane sulfonate and alkyl sulfates are employed in amounts of from about 0.04 to about 0.4% by weight, preferably from about 0.1 to about 0.14% by weight.

Any of the well known alkyl ether sulfates having from about 10 to about 14 carbon atoms in the form of alkali metal, alkaline earth metal, ammonium or substituted ammonium, e.g., such as those described above for the alkane sulfonates and alkyl sulfates, salts or mixtures thereof can be used. Such sulfates are commercially available or can be prepared by well known procedures. The alkyl ether sulfates preferably are employed in amounts of from about 0.01% to about 0.1% by weight of the aqueous disinfectant composition, preferably about 0.03% by weight. Preferred alkyl ether sulfates are sodium lauryl ether sulfate having 2 to 3 moles of ethylene oxide, sodium lauryl myristyl ether sulfate, sodium lauryl ether sulfate and sodium laureth-8 sulfate+sodium oleth ether sulfate, as well as magnesium lauryl ether sulfate, monoisopropylamine lauryl ether sulfate+cocamide DEA and ammonium lauryl ether sulfate and triethanolamine lauryl ether sulfate and those of the "Texapon" variety.

The mixture of the alkane sulfonate and/or alkyl sulfate with the alkyl ether sulfate should be used in an amount which will preclude excessive build up thereof on the treated surface, i.e., generally no more than about 0.5% by weight of the aqueous disinfectant composition. Suitably the amount will be from about 0.05 to about 0.5% by weight, preferably about 0.15% by weight.

The weight ratio of alkane sulfonates or alkyl sulfates to alkyl ether sulfates is also important. It must be within a range of 10:1 to 2:1; and preferably about 4:1. The particular ratio selected should provide an optimization of sufficient or complete wetting and, thus, reliable efficacy and effective foam formation. Alkane sulfonates have good foaming properties. However, their foam formation is retarded by water hardeners. Therefore, a certain amount of ether sulfate is needed to stabilize the foam. However, too high a ratio, i.e., more than about 2:1, brings about excessive foaming and, therewith, inclusion of too much air and, consequently, an uncertain complete wetting of the surface.

Contrary to nonionic surfactants, the mixture of alkane sulfonate and/or alkyl sulfate with alkyl ether sulfate has no tendency to cause stress corrosion on plexiglass.

The weight ratio of the alcoholic component, i.e., the mixture of ethyl alcohol and isopropyl alcohol, to the anionic surfactant component, i.e., the mixture of alkane sulfonate and/or alkyl sulfate with alkyl ether sulfate, is important and should be in the range of from about 300:1 to about 50:1, preferably about 100:1 to about 200:1. The latest conventional sprayable disinfectants contain ratios of alcohol to wetting agent of 450 to 700:1, the wetting agent used most being nonionic. Therefore, they have no distinct cleansing power. At ratios lower than 50:1 the question of residues becomes acute.

The pH of the aqueous disinfectant composition of the invention should be in the range of 2 to 6 or 8 to 12. Therefore, a pH adjusting agent, i.e., an acidifying or alkalizing agent, is required. Adjustment in the acidic range, i.e., pH 2 to 6 preferably is achieved with an organic acid, more preferably with a so-called edible acid such as malic acid, citric acid and tartaric acid. The amount of edible acid employed generally will be from about 0.05 to about 0.18% by weight. However, inorganic acids may also be used. A pH of about 3.5 can be achieved, for example, by addition of about 0.13% by weight of malic acid, a preferred acid. Adjustment in the alkaline range, i.e., pH 8 to 12, can be achieved with any suitable alkalizing agent, ammonium hydroxide solution being preferred. Generally the amount of ammonium hydroxide solution employed will provide from about 0.05 to about 0.15% by weight of ammonia. For example, addition of about 0.45% by weight of a 25% aqueous solution of ammonia will provide a pH of 10.5 to 11. The particular pH chosen will depend on the specific formulation and its intended end-use.

The water employed as an essential ingredient in the aqueous disinfectant composition of the invention preferably is demineralized water.

In addition to the essential ingredients of the aqueous disinfectant composition, there may be included therein optional ingredients such as are conventional, for example, corrosion inhibitors, dyes, perfumes and odorants. However, in order to avoid the possibility of allergenic reaction, any corrosion inhibitor, dye, perfume or odorant to be included should be kept at as low a concentration as possible. Preferably such additives should, if possible, be skin compatible.

The aqueous disinfectant compositions of the invention can be prepared by mixing the various ingredients in water and providing agitation until a homogeneous liquid results. Conveniently, the ethyl and isopropyl alcohols are dissolved in the water and the surfactants, pH adjuster and any optional ingredients are then added sequentially with stirring.

The invention is illustrated by the following specific embodiments but is not restricted thereto.

EXAMPLE 1

An aqueous surface disinfectant composition was prepared having the following composition:

| Ingredient | % by weight |
| --- | --- |
| Ethyl Alcohol | 12.5 |
| Isopropyl alcohol | 17.5 |
| Sodium $C_{12}-$ to $C_{16}-$ alkane sulfonate | 0.25 |
| Sodium $C_{12}-$ to $C_{14}-$ alkyl ether sulfate | 0.05 |
| Malic acid | 0.1 |
| Demineralized water qs to | 100. |

The aqueous disinfectant composition of Example 1 can be readily sprayed. It was applied to the surfaces to be disinfected and wiped off after about 2.5 minutes. Studies carried out in accordance with the DGHM (German Association for Hygiene and Microbiology) guidelines confirmed that the disinfectant composition of Example 1, which takes about 2.5 minutes to act, was suitable for hospital prophylaxis. Long term testing on plastic surfaces such as polyacrylate glass showed no impairment of the surface.

EXAMPLE 2

An aqueous surface disinfectant composition containing 15% ethyl alcohol and 10% isopropyl alcohol was prepared by adding to the aqueous alcoholic component a mixture of a secondary alkane sulfonate having 12 to 16 carbon atoms in an amount of 0.12% by weight and the triethanolamine salt of $C_{12}$- to $C_{14}$-alkyl ether sulfate in an amount of 0.03% by weight together with 0.4% by weight of a 25% $NH_4OH$ solution. The resulting composition had a pH of 10.5 to 11 and showed otherwise the same characteristics as the disinfectant composition of Example 1.

Both the composition of Examples 1 and 2 were tested in accordance with the requirements which must be met to be included in the 7th list of disinfection methods tested by the "Guidelines for Testing Chemical Disinfectants" and are accepted as effective by the German Association for Hygiene and Microbiology (DGHM). These tests indicated that, surprisingly, time for the disinfectant to act was reduced substantially below 15 minutes.

The efficacy of the aqueous disinfectant composition of the invention as a surface disinfectant for hospital prophylaxis and general practice was demonstrated using the following tests:

1. qualitative suspension test
2. quantitive suspension test with and without 0.2% albumin loading
3. microorganism carrier test using standard cotton fabric
4. quantitative surface test.

The following strains were used as test strains:

| | | |
|---|---|---|
| Staphyloccoccus aureus | ATCC | 6538 |
| Escherichia coli | ATCC | 11229 |
| Pseudomonas aeruginosa | ATCC | 15442 |
| Proteus mirabilis | ATTCC | 14153 |
| Candida albicans | ATCC | 10231 |

In all the tests, the subcultures were treated for the purpose of inactivation with 3.0% of an emulsifier (Tween 80), 3.0% of saponin, 0.1% of histidine and 0.1% of cystein (TSHC).

The tables below give the results of the tests with the preparation from Example 1 (TPH 5221).

In a qualitative suspension test, as shown in Table 1, all test microorganisms were exterminated within 30 seconds.

Table 2 indicates that in the quantitative suspension test a logarithmic reduction factor (log RF) of 5 log steps was reached within one minute for all the test microorganisms and that it was possible in each case to stay within the limit of detection.

In the microorganism carrier test using standard cotton (Table 3), no microorganisms capable of proliferation could be detected after 30 minutes for Staphylococcus aureus, after 15 minutes for Candida albicans and after 5 minutes for any other microorganisms.

In the quantitative surface test on plastics (PVC) and tiles (see Tables 4, 4a and 4b), *Staphylococcus aureus* is somewhat more resistant than *Escherichia coli* and *Pseudomonas aeruginosa*. With the latter, a reduction factor of 5 log steps was reached in one minute, with the former after 2 and with *Staphylococcus aureus* after about 2½ minutes.

A quantitative surface test with reference to DGHM guidelines, but on acrylate glass, also was performed taking account of the special requirements of solariums. In this case a reduction factor of more than 5 log steps was reached after one minute on the tested microorganisms *Staphylococcus aureus, Pseudomonas aerusinosa* and *Candida albicans*, as can be seen from Table 5.

TABLE 1

Preparation: TPH 5221
Qualitative suspension test
Time to act in minutes

| | Staph. aureus | | | | | E. Coli | | | | | Ps. aeruginosa | | | | | Prot. mirabilis | | | | | Candida albicans | | | | |
|---|---|---|---|---|---|---|---|---|---|---|---|---|---|---|---|---|---|---|---|---|---|---|---|---|---|
| Conc. in % | 0.5 | 1 | 2 | 2.5 | 5 | 0.5 | 1 | 2 | 2.5 | 5 | 0.5 | 1 | 2 | 2.5 | 5 | 0.5 | 1 | 2 | 2.5 | 5 | 0.5 | 1 | 2 | 2.5 | 5 |
| 100.0 | − | − | − | − | − | − | − | − | − | − | − | − | − | − | − | − | − | − | − | − | − | − | − | − | − |
| GC | + | + | + | + | + | + | + | + | + | + | + | + | + | + | + | + | + | + | + | + | + | + | + | + | + |

− indicates no growth
+ indicates growth
GC = growth control
Inactivation: TSHC

TABLE 2

Preparation: TPH 5221
Concentration: 100.0%
Quantitative suspension test
Time to act in minutes

| | without albumin | | | | with 0.2% of albumin | | | |
|---|---|---|---|---|---|---|---|---|
| | 1 | 2 | 2.5 | 3 | 1 | 2 | 2.5 | 3 |
| Staph. aureus | ≧5.60 | ≧5.11 | ≧5.30 | ≧5.23 | ≧5.60 | ≧5.11 | ≧5.30 | ≧5.23 |
| Control | 6.60 | 6.11 | 6.30 | 6.23 | 6.60 | 6.11 | 6.30 | 6.23 |
| Pseud. aeruginosa | ≧5.34 | ≧5.18 | ≧5.28 | ≧5.21 | ≧5.34 | ≧5.18 | ≧5.28 | ≧5.21 |
| Control | 6.34 | 6.18 | 6.28 | 6.21 | 6.34 | 6.18 | 6.28 | 6.21 |
| Candida Albicans | ≧5.15 | ≧5.21 | ≧4.98 | ≧5.17 | ≧5.15 | ≧5.21 | ≧4.98 | ≧5.17 |
| Control | 6.15 | 6.21 | 5.98 | 6.17 | 6.15 | 6.21 | 5.98 | 6.17 |

TABLE 2-continued

Preparation: TPH 5221
Concentration: 100.0%
Quantitative suspension test
Time to act in minutes

| | without albumin | | | | with 0.2% of albumin | | | |
|---|---|---|---|---|---|---|---|---|
| | 1 | 2 | 2.5 | 3 | 1 | 2 | 2.5 | 3 |
| Initial microbial count: | Staph. aereus | | | | $6 \times 10^9$ ml | | | |
| | Ps. aeruginosa | | | | $4.5 \times 10^9$ ml | | | |
| | C. albicans | | | | $1 \times 10^9$ ml | | | |

Data are given in logarithmic reduction factors (log RF)
Inactivation: TLSH

TABLE 3

Preparation: TPH 5221
Microorganism carrier test with standard cotton
Time to act in minutes

| | Staph. aureus | | | | | E. coli | | | | | Ps. aeruginosa | | | | | Prot. mirabilis | | | | | Candida albicans | | | | |
|---|---|---|---|---|---|---|---|---|---|---|---|---|---|---|---|---|---|---|---|---|---|---|---|---|---|
| Conc. % | 5 | 15 | 30 | 60 | 120 | 5 | 15 | 30 | 60 | 120 | 5 | 15 | 30 | 60 | 120 | 5 | 15 | 30 | 60 | 120 | 5 | 15 | 30 | 60 | 120 |
| 100.0 | + | + | − | − | − | − | − | − | − | − | − | − | − | − | − | − | − | − | − | − | − | − | − | − | − |
| GC | + | + | + | + | + | + | + | + | + | + | + | + | + | + | + | + | + | + | + | + | + | + | + | + | + |

− indicates no growth
+ indicates growth
GC = growth control
Inactivation: TSHC

TABLE 4

Preparation TPH 5221
Time to act in minutes
Quantitative surface test
Data are given in logarithmic
Reduction factors (Log RF)

| | | PVC | | | | | Tiles | | | | |
|---|---|---|---|---|---|---|---|---|---|---|---|
| Test microorganism | Conc. in % | 1 | 2 | 2.5 | 3 | 5 | 1 | 2 | 2.5 | 3 | 5 |
| Staphyloccocus aureus | 100.0 | 4.83 | ≧5.81 | ≧5.85 | ≧5.18 | ≧5.22 | 3.41 | 4.75 | ≧5.15 | ≧5.14 | ≧5.27 |
| First control | log | 6.94 | 6.81 | 6.85 | 6.18 | 6.22 | 6.33 | 6.30 | 6.15 | 6.14 | 6.27 |
| Second control | log 7.96 | | | | | | | | | | |

Initial microbial count = $7 \times 10^9$ ml
Temp.: 22° C.
Rel. humidity: 46%
Inactivation: TLSH

TABLE 4a

Preparation TPH 5221
Time to act in minutes
Quantitative surface test
Data are given in logarithmic
Reduction factors (Log RF)

| | | PVC | | | | | Tiles | | | | |
|---|---|---|---|---|---|---|---|---|---|---|---|
| Test microorganism | Conc. in % | 1 | 2 | 2.5 | 3 | 5 | 1 | 2 | 2.5 | 3 | 5 |
| Escherichia coli | 100.0 | 4.46 | ≧5.23 | ≧5.48 | ≧5.17 | ≧5.22 | 3.68 | ≧5.81 | ≧5.82 | ≧5.69 | ≧5.10 |
| First control | log | 6.34 | 6.23 | 6.48 | 6.17 | 6.22 | 6.42 | 6.81 | 6.82 | 6.69 | 6.10 |
| Second control | log 7.14 | | | | | | | | | | |

Initial microbial count = $4.5 \times 10^9$ ml
Temp.: 22°C.
Rel. humidity: 46%
Inactivation: TLSH TABLE 4b Preparation: TPH 5221
Time to act in minutes
Quantitative surface test
All data are given in logarithmic
reduction factors (log RF)

| Test micro-organism | Conc. in % | PVC | | | | | Tiles | | | | |
|---|---|---|---|---|---|---|---|---|---|---|---|
| | | 1 | 2 | 2.5 | 3 | 5 | 1 | 2 | 2.5 | 3 | 5 |
| Pseudomonas aeruginosa | 100.0 | ≧5.36 | ≧5.78 | ≧5.23 | ≧5.20 | ≧5.26 | ≧5.42 | ≧5.54 | ≧5.25 | ≧5.37 | ≧5.48 |
| First control | log | 6.36 | 6.78 | 6.23 | 6.20 | 6.26 | 6.42 | 6.54 | 6.25 | 6.37 | 6.48 |
| Second control | log 7.39 | | | | | | | | | | |

Initial microbial count = $3 \times 10^9$ ml
Temp.: 22°C.
Rel. humidity: 46%
Inactivation: TLSH The composition of Example 1 was studied in a quantitative surface test on plexiglass; the action time in minutes and the data in logarithmic reduction factors (RF) are give in Table 5 below

TABLE 5

| Test micro-organism | | PLEXIGLASS | | |
|---|---|---|---|---|
| | conc. in % | 1 | 2 | 2.5 |
| Staph. aureus | 100.0 | >6.37 | >6.11 | >6.02 |
| control | WHS | 7.37 | 7.11 | 7.02 |
| Ps. aeruginosa | 100.0 | >5.52 | >5.61 | >5.42 |
| Control | WHS | 6.52 | 6.61 | 6.42 |
| Cand. albican | 100 0 | >5.48 | >5.06 | >4.98 |
| Control | WHS | 6.48 | 6.06 | 5.98 |
| Initial microabial count: | Staphyloccocus aureus = $5.0 \times 10^9$/ml Pseudomonas aeruginosa = $2.4 \times 10^9$/ml Candida albicans = $1/5 \times 10^8$/ml | | | |

DEACTIVATION TSHC

In the case of a composition comprising ethyl alcohol as the sole alcohol component in an amount of 30% by weight, and the remainder of the formulation being, for example, a surfactant mixture in an amount of 0.15% by weight and malic acid in an amount of about 0.10 to 0.15% by weight, the remainder being water, the formulation acted in a quantitative suspension test only in 5 minutes and the flashpoint was 27° C. When the ethyl alcohol content was increased to 40% by weight, the time to act in the suspension test improved to 3 minutes, but the flashpoint decreased to 24° C. When the ethyl alcohol content was 50% by weight, the flashpoint was 20° C. and therefore unsuitable because in order to comply with the "Safety Regulation for Avoiding the Danger of Fires and Explosions Caused by Alcoholic Disinfectants; ZH 1/598 of the Employer'Liability Insurance Association (FRG), the flashpoint of an alcoholic spray disinfectant must be 24° C. or higher (according to DIN 51755).

The aqueous disinfectant compositions can be applied to the surface to be disinfected using any of the conventional techniques and applicators. Thus, for example, they can be sprayed from a container fitted with a conventional pump spray device or they can be formulated for application as an aerosol spray.

We claim:

1. An aqueous surface disinfectant composition consisting essentially of
   a) from about 20 to about 35% by weight of a mixture of ethyl alcohol and isopropyl alcohol in a weight ratio of ethyl alcohol to isopropyl alcohol of from about 1:2 to about 2:1;
   b) from about 0.05 to about 0.5% by weight of a mixture of anionic surfactants consisting of
      b-1) a salt of a primary or secondary alkane sulfonic acid or alkyl sulfate having from 10 to 18 carbon atoms in the alkane and alkyl radicals, and
      b-2) a salt of an alkyl ether sulfate having from 10 to 14 carbon atoms in the alkyl radical;
   c) an alkalizing agent or an acidifying agent selected from the group consisting of malic, citric or tartaric acid; said agents being present in an amount sufficient to provide a pH within the range of from about 2 to about 6 or about 8 to about 12;
   d) and the remainder to 100% by weight of water; wherein the weight ratio of (b-1) to (b-2) is from about 10:1 to 2:1 and of (a) to (b) is from about 300:1 to about 50:1 and is sprayable.

2. The composition of claim 1 wherein the salt of the alkane sulfonic acid, the alkyl sulfate and the alkyl ether sulfate is an alkali metal, alkaline earth metal, ammonium or substituted ammonium salt.

3. The composition of claim 2 wherein the acidifying agent is an edible organic acid and the alkalizing agent is ammonia.

4. The composition of claim 3 wherein the edible acid is malic acid, citric acid or tartaric acid.

5. The composition of claim 4 comprising from about 25 to about 30% by weight of a mixture of ethyl alcohol and isopropyl alcohol in a weight ration of ethyl alcohol to isopropyl alcohol of rom about 1.5:1 to about 1:1.4, 0.15% by weight of the mixture of anionic surfactants, wherein the ratio of the salt of the primary or secondary alkane sulfonic acid or alkyl sulfate to the salt of the alkyl ether sulfate is from about 4:1, to about 5:1 and of the mixture of ethyl alcohol and isopropyl alcohol to the mixture of anionic surfactants is from about 100:1 to about 200:1.

6. The composition of claim 5 comprising by weight of the composition about 12.5% of ethyl alcohol, about 17.5% of isopropyl alcohol, about 0.25% of sodium $C_{12}$- to $C_{16}$-alkane sulfonate, about 0.05% of sodium $C_{12}$- to $C_{14}$-alkyl ether sulfate, about 0.1% of malic acid and the remainder of 100% water.

7. The composition of claim 5 comprising by weight of the composition about 15% of ethyl alcohol, about 10% of isopropyl alcohol, about 0.12% by weight of the salt of the secondary $C_{12}$- to $C_{16}$-alkane sulfonic acid, about 0.03% of triethanolammonium $C_{12}$- to $C_{14}$-alkyl ether sulfate, about 0.1% of ammonia and the remainder to 100% water.

* * * * *

UNITED STATES PATENT OFFICE
CERTIFICATE OF CORRECTION

PATENT NO. : 5,122,541
DATED : June 16, 1992
INVENTOR(S) : Heinz Eggensperger, et al It is certified that error appears in the above-identified patent and that said Letters Patent is hereby corrected as shown below:

Column 10, line 60 should read: --remainder to 100% water.--

Signed and Sealed this

Twenty-first Day of September, 1993

Attest:

BRUCE LEHMAN

Attesting Officer

Commissioner of Patents and Trademarks